United States Patent [19]
Reeve

[11] Patent Number: 6,001,615
[45] Date of Patent: Dec. 14, 1999

[54] ENZYMATIC REDUCTION OF KETONE GROUPS IN 6-CYANO-3,5-DIHYDROXY-HEXANOIC ALKYL ESTER

[75] Inventor: Christopher David Reeve, Middlesbrough, United Kingdom

[73] Assignee: Zeneca Limited, London, United Kingdom

[21] Appl. No.: 08/981,731

[22] PCT Filed: Jun. 17, 1996

[86] PCT No.: PCT/GB96/01422

§ 371 Date: Dec. 23, 1997

§ 102(e) Date: Dec. 23, 1997

[87] PCT Pub. No.: WO97/00968

PCT Pub. Date: Jan. 9, 1997

[30] Foreign Application Priority Data

Jun. 23, 1995 [GB] United Kingdom .................... 9512837

[51] Int. Cl.$^6$ .................................................. C12P 13/00
[52] U.S. Cl. ........................................... 435/128; 435/280
[58] Field of Search ........................................ 435/280, 128

[56] References Cited

U.S. PATENT DOCUMENTS

| 5,026,642 | 6/1991 | Radunz et al. ......................... 435/117 |
| 5,155,251 | 10/1992 | Butler et al. . |
| 5,324,662 | 6/1994 | Patel et al. .............................. 435/280 |

FOREIGN PATENT DOCUMENTS

| 330 172 | 8/1989 | European Pat. Off. . |
| 569 998 | 11/1993 | European Pat. Off. . |

OTHER PUBLICATIONS

Chemical Abstracts, vol. 120, No. 5, Jan. 31, 1994, abstract No. 52720, Patel, R et al: "Enantioselective microbial reduction of 3,5–dioxo–6–(benzyloxy)hexanoic acid, ethyl ester" XP002016585, see abstract & Enzyme Microb, Techno. (1993), 15(12), 1014–21 CODEN:EMTED2; 0141–0229, 1993.

Zelinski et al: "Purification and characterization of a novel carbonyl reductase isolated from *Rodococcus erythropolis*", Journal of Biotechnology, 33(3), 283–91.

Tetrahedron(1994), 51(3), 687–94 ; Nakamura et al:"Mechanistic study for sterochemical control of microbial reduction of alpha–keto esters in an organic solvent".

*Primary Examiner*—Sandra E. Saucier
*Attorney, Agent, or Firm*—Pillsbury Madison & Sutro LLP

[57] ABSTRACT

A compound of formula (III)

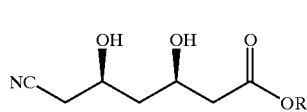

is produced by selectively reducing a compound of formula (II)

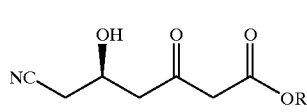

using a reductase possessing the properties of one produced by Beauveria, Candida, Kluyveromyces, Torulaspora or Pichia.

or

A compound of formula

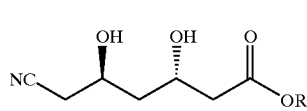

is produced by selectively reducing a compound of formula II using a reductase possessing the properties of one produced by *Candida pelliculosa*, *Neurospora crassa*, *Pichia trehalophila* or preferably *Hansenula anomola*.

10 Claims, 1 Drawing Sheet

ENZYMATIC REDUCTION OF KETONE GROUPS IN 6-CYANO-3,5-DIHYDROXY-HEXANOIC ALKYL ESTER

THIS INVENTION relates to the reduction of ketone groups.

It is known from Brower et al. Tetrahedron letters 1992, pages 2279–2282 to synthesise a compound of formula

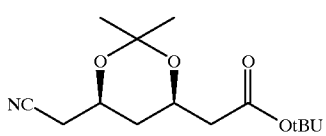
(I)

by diastereoselective reduction of a compound of formula

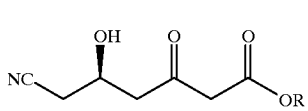
(II)

using the method of Chen et al, Tetrahedron Letters 1987 28 155 and Chem Lett 1987 1923 followed by protection as the acetonide. A cross Claisen approach to compound (1) was also reported. These routes involved the use of temperatures of $-90°$ C., which renders them expensive and inconvenient.

BRIEF DESCRIPTION OF THE DRAWING

The drawing is a graph showing the concentrations of compounds I and II at times up to about 50 hours during the reaction of Example 13.

Compound (1) may be used as an intermediate in the synthesis of CI-981, an inhibitor of HMG CoA reductase which reduces total plasma and low density lipoprotein cholesterol in man. Its key structural feature may also be derived from a compound of formula

Figure 1:
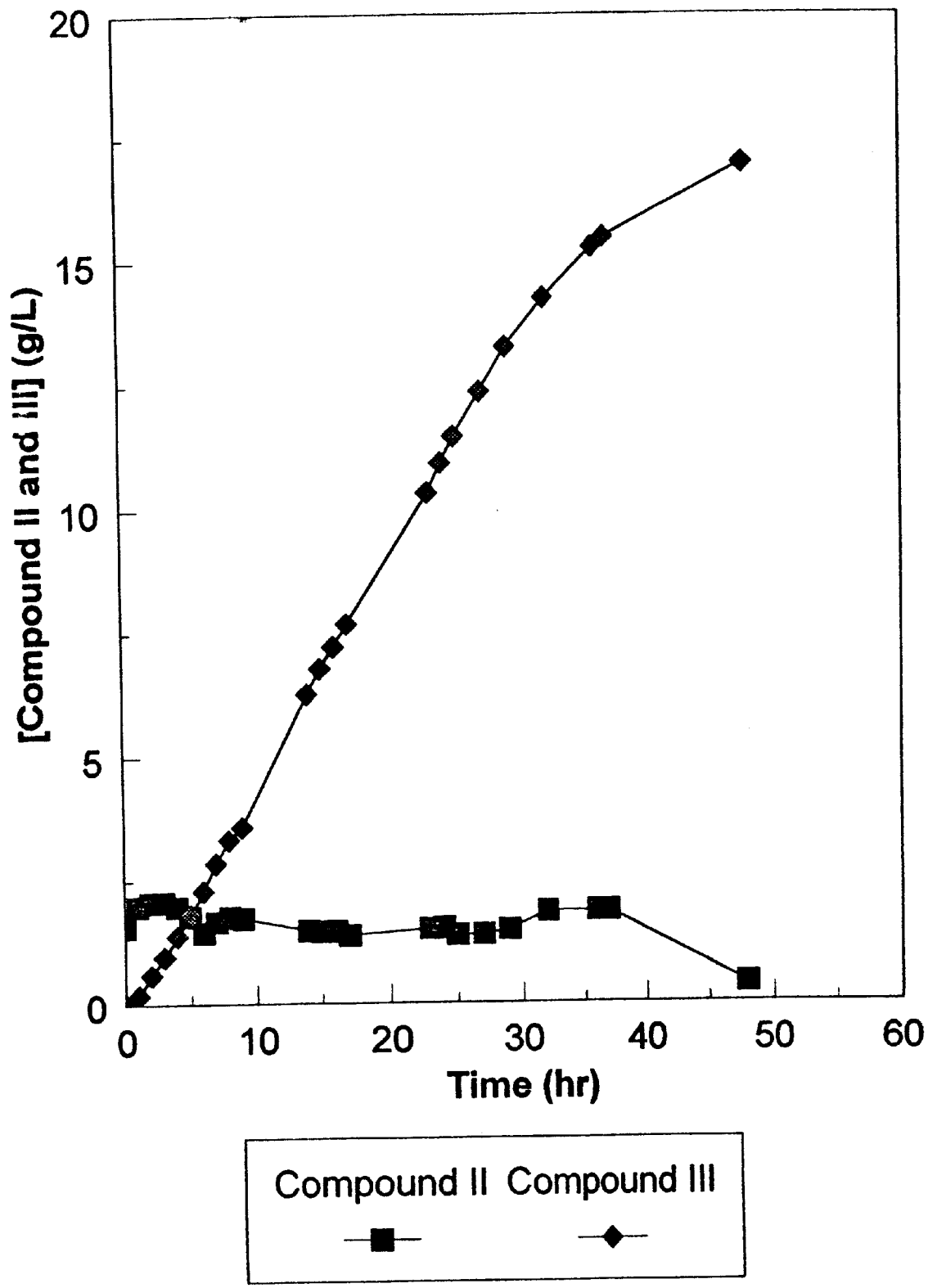

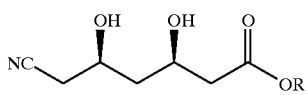
(III)

In the above formula R is an alkyl group, preferably having 1 to 6 carbon atoms and is more preferably a t-butyl group.

We have found that compound (III) may be produced by reduction of compound (II) with moderate to high selectivity and at convenient temperatures using a ketone reductase commonly found among species of the genera Beauveria, Pichia, Candida, Kluyveromyces, and Torulaspora but that in each genus exceptions may occur or possibly the enzyme will be accompanied by one of opposite stereospecificity.

The invention therefore comprises producing a compound of formula (III) by selectively reducing a compound of formula (II)

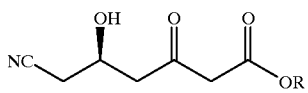

using a reductase possessing the properties of those produced by a microorganism selected from Beauveria preferably *Beauveria bassiana*, Pichia preferably *Pichia pastoris, haplophila* or *membranefaciens*, Candida preferably *Candida humicola, solani, diddenssiae* or *friedrichii*, Kluyveromyces preferably *Kluyveromyces drosophilarum*, or Torulaspora preferably *Torulaspora hansenii* and preferably *Pichia angusta*.

The invention also comprises producing a compound of formula (III) by selectively reducing a compound of formula (II) using whole cells of or extracts from the said microorganisms preferably *Beauveria bassiana, Pichia pastoris, Pichia haplophila, Pichia membranefaciens, Candida humicola, Candida solani, Candida diddensiae, Candida friedrichii, Kluyveromyces drosophilarum, Torulaspora hansenii* or preferably *Pichia angusta*.

The invention is preferably carried out using whole cells of the organism as this avoids the need to separate the desired enzyme and provides co-factors necessary for the reaction.

Any of the above species may be used but in order to obtain high conversions and high selectivity it is preferred to use the enzyme or whole cells of *Pichia haplophila*, or more preferably *Pichia angusta*.

In general a co-factor, normally AND(P)H (nicotinamide adenine dinucleotide or nicotinamide adenine dinucleotide phosphate) and a system for re-generating the co-factor, for example glucose and glucose dehydrogenase, are used with the enzyme to drive the reaction. As suitable co-factors and reduction mechanisms are present in the whole cells it is preferred to use the whole cells in a nutrient medium which preferably contains a suitable carbon source, which may include one or more of the following: a sugar, e.g. maltose, sucrose or preferably glucose, a polyol e.g. glycerol or sorbitol, citric acid, or a lower alcohol, for example methanol or ethanol.

If whole cells are intended to grow during the reaction nitrogen and phosphorus sources and trace elements should be present in the medium. These may be those normally used in culturing the organism.

The process may be carried out by adding a compound of formula II to a culture of the growing organism in a medium capable of supporting growth or to a suspension of the live cells in a medium which preferably contains a carbon source but which lacks one or more nutrients necessary for growth. Dead cells may also be used providing the necessary enzymes and co-factors are present; if necessary they may be added to the dead cells.

If desired the cells may be immobilised on a support which is contacted with compound of formula II preferably in the presence of a suitable carbon source as previously described.

The pH is suitably 3.5 to 9, for example 4 to 9, preferably at most 6.5 and more preferably at most 5.5. Very suitably a pH of 4 to 5 is used. The process may suitably be carried out at a temperature of 10 to $50°$ C., preferably 20 to $40°$ C. and more preferably 25 to $35°$ C. It is preferred to operate under aerobic conditions if live whole cells of the aforesaid organisms are present. An aeration rate equivalent to 0.01 to 1.0 volumes of oxygen measured at standard temperature and pressure per volume of the culture medium per minute is suitably employed at the aforesaid conditions of pH and temperature but it will be appreciated that considerable variation is possible. The oxygen may be supplied as air. Similar pH temperature and aeration conditions may be used during growth of the organisms if this is carried out separately from the process.

Purified enzymes may be isolated by known means suitably by centrifuging a suspension of disintegrated cells and separating a clear solution from debris, separating the desired enzyme from the solution for example by ion exchange chromatography suitably with elution from the column with liquid of increasing ionic strength and/or by selective precipitation by the addition of an ionic material, for example ammonium sulphate. Such operations may be repeated if desired to enhance purity.

EXAMPLE 1

Preparation of the Compound of Formula (III)

Microorganisms were maintained on YM (Oxoid Company) agar plates prepared by dissolving 41 g of yeast and mold agar in 1 L of distilled water and sterilizing in an autoclave.

For growth in liquid medium a loopful of microbial cells was aseptically transferred from an agar plate to a 1 L baffled flask containing 200 ml of mineral salts medium of composition (per liter) $K_2HPO_4$ (1.9 g), $NaH_2PO_4.2H_2O$ (2.02 g) $(NH_4)_2SO_4$ (1.8 g), $MgSO_4\ 7H_2O$ (0.2 g), $FeCl_3$ (0.97 mg) and trace elements solution (1 ml). Trace elements solution consisted of (per liter) $CuSO_4.5H_2O$ (0.02 g), $MnSO_4.4H_2O$ (0.1 g), $ZnSO_4.7H_2O$ (0.1 g) and $CaCO_3$ (1.8 g). The minimal medium was supplemented with 0.2% (w/v) yeast extract and 2.25% (w/v) glucose.

Microorganisms were grown at 28° C. on an orbital shaker at 150 rpm for 24–48 hours.

Microbial cells were harvested by centrifuging at 7000 rpm for 20 minutes at 10° C. The cell pellet was resuspended in 100 ml of 50 mM sodium phosphate buffer, pH 6.4 and the cells washed by centrifuging as above. The cell pellet was finally resuspended in 50 ml of the above buffer.

To the 50 ml of cell suspension in a 250 ml baffled flask was added glucose (10 g per liter) and the compound of formula II (2 g per liter). The cells were incubated at 28° C. on a rotary shaker at 150 rpm for 18–24 hours.

The entire reaction broth was extracted with 2×1 volume of ethyl acetate. In many cases an emulsion was formed which was broken by centrifuging at 10,000 rpm for 5 minutes at 28° C. The pooled ethyl acetate extracts were dried over anhydrous sodium sulphate and the solvent removed by vacuum distillation to afford a golden oil.

The extent of conversion of the compound of formula II to the compound of formula III and the enantiomeric composition of the compound of formula III was determined by HPLC (high pressure liquid chromatography). The conditions for HPLC are described below:

HPLC: Waters 590 programmable pump.

Column: "Chiralcel" OJ (250mm×4.6mm) (Chiracel is a trade mark of Diacel Chemical Industries Ltd) with a Guard Column 50mm×4.6mm of 10 μm Particle size.

Solvent: Hexane; Ethanol (95:5)

Flow Rate: 1 ml min$^{-1}$

Temperature: Ambient

Detection: Refractive Index Waters differential refractometer R401

The retention times of the compounds of formula II, III and the diastereoisomer of III, IV were 43 minutes, 27 minutes and 21 minutes respectively.

The results obtained are summarised in Table 1.

TABLE 1

| Microorganism | Conversion (%) | Ratio of Compound III:IV |
| --- | --- | --- |
| Beauveria bassiana ATCC 7159 | 34 | 17:1 |
| Candida humicola CBS 1897 | 8 | >20:1* |
| Candida diddensiae ATCC 20213 | 2 | >20:1* |
| Candida frieddrichii ATCC 22970 | 3 | >20:1* |
| Candida solani CBS 1908 | 7 | 12:1 |
| Hansenula nonfermentans CBS5764 | 75 | 1.8:1 |
| Kluyveromyces drosophilarum CBS 2105 | 5 | 6:1 |
| Pichia angusta NCYC 495 | 100 | 110:1 |
| Pichia angusta NCYC R320* | 98 | >100:1* |
| Pichia angusta NCYC R322* | 98 | >100:1* |
| Pichia haplophila CBS 2028 | 97 | 33:1 |
| Pichia membranefaciens DSM 70366 | 4 | >20:1* |
| Pichaa pastoris BPCC 260 | 20 | >20:1* |
| Pichia pastoris BPCC 443 | 17 | >20:1* |
| Pichia pastoris NCYC R321+ | 20 | >20:1* |
| Torulaspora hansenii ATCC 20220 | 17 | >20:1* |

*Compound IV not detected. Results based on detection limit for compound IV.
+Deposited under the provisions of the Budapest Treaty on 18 May 1995.

EXAMPLE 2

Preparation of the Compound IV, the Diastereoisomer of Compound of Formula III $$\text{NC} \diagup\diagdown\underset{\overline{OH}}{\diagup}\diagdown\underset{\overline{OH}}{\diagup}\diagdown\diagup\underset{O}{\diagdown}\text{OR} \quad (IV)$$

Microorganisms were maintained and grown as described in Example 1. The biotransformation and analysis was also performed exactly as described in Example 1.

The results are summarised in Table 2.

TABLE 2

| Microorganism | Conversion (%) | Ratio of Compound IV:III |
| --- | --- | --- |
| Candida pelliculosa ATCC 2149 | 98 | 9:1 |
| Hansenula CBS 2230 | 85 | 37:1 |
| Neurospora crassa ATCC 9277 | 58 | 10:1 |
| Pichia trehalophila CBS 5361 | 65 | 3:1 |

It will be seen from the above results that certain members of each genus Candida and Pichia produce both diastereoisomers. The specificity of for example Pichia angusta on the one hand and Hansenula anomola on the other for different diastereoisomers indicates the existence of two enzymes of opposite stereospecificity and both and/or a further enzyme of lesser stereo-specificity may be present in some species.

EXAMPLE 3

Growth of Pichia Angusta NCYC R320 in Fermenters and In Situ Preparation of the Compound of Formula (III) (R=t-butyl)

Pichia angusta NCYC R320 was grown in both batch and fed-batch culture in a Braun Biostat ED/ER5 L fermenter.

Growth in batch culture was performed in 5 L of medium of composition (per liter) glucose, 40 g; $MgSO_4\ 7H_2O$, 1.2 g; $K_2SO_4$, 0.21 g; $KH_2PO_4$, 0.69 g; $H_3PO_4$ (17M), 1 ml;

yeast autolysate, 2 g; FeSO$_4$ 7H$_2$O, 0.05 g; polypropylene glycol antifoam, 0.3 ml; trace element solution, 2 ml. The trace element solution comprises (per liter) ZnSO$_4$ 7H$_2$O, 10 g; MnSO$_4$ 4H$_2$O, 10 g; CuSO$_4$ 5H$_2$O, 1 g and H$_3$PO$_4$ (11.6M), 1 ml. The medium was prepared in tap water. The medium was adjusted and controlled at the desired pH by addition of 7M NH$_4$OH.

Growth in fed-batch culture was performed as described for batch culture except that when the glucose concentration had decreased to <10g/L, 1 L of the fermentation broth was aseptically removed and 1 L of medium of composition (per liter) glucose, 240 g; yeast autolysate, 7 g; FeSO$_4$ 7H$_2$O, 0.175 g, polypropylene glycol antifoam, 1 ml and trace element solution, 7 ml, was fed in at a rate sufficient to maintain the glucose concentration in the range 2 to 5 g/L.

Fermentations performed under both batch and fed-batch culture were initiated by the addition of an inoculum of *Pichia angusta* NCYC R320. The inoculum was prepared in 200 ml of the mineral salts medium described in Example 1 and was grown at 28° C. on an orbital shaker at 150 rpm for 18–20 hours. Prior to inoculation of the fermenter the inoculum was diluted 10-fold in sterile medium of the same composition.

Fermentations were performed under the following conditions of pH, temperature, aeration and agitation until a dry cell weight in the range 10 to 15 g/L was obtained:
Temperature: 28, 34, 400° C.
pH: 4.5, 5.5, 6.5
Aeration: 0.1, 1.0 vvm (volume air per volume of medium per minute)
Agitation: 600 rpm The preparation of the compound of formula (III) (R=t-butyl) was initiated by the addition of the compound of formula II (R=t-butyl) as a crude oil of approximately 65% w/w concentration the balance being substantially t-butyl aceto acetate. The compound of formula (II) (R=t-butyl) was added as a continuous feed at a rate sufficient to maintain its concentration at typically 1 to 5 g/L, preferably at 2 g/L. Solid glucose was added to the fermentation broth as cosubstrate to maintain a concentration of 1 to 5 g/L. In each experiment the preparation of the compound of formula (III) (R=t-butyl) was performed under the same conditions of temperature, pH, aeration and agitation as for the growth stage of the microorganism.

The concentration of the compounds of formula (II) (R=t-butyl) and (III) (R=t-butyl) in the fermentation broth were measured by reverse phase HPLC. The conditions for HPLC are described below:
HPLC: Hewlett Packard HP 1050
Column: Waters Nova-Pak® C18 column 3.9×300mm dimension and 4 μm particle size. Nova-Pak is a registerd trademark of Millipore Corporation.
Solvent: 0.02M phosphoric acid in water:acetonitrile (60:40)
Flow rate: 1 ml/min
Detector: Hewlett Packard HP 1047A refractive index detector
Temperature: Ambient
The retention times of the compounds of formula (II) (R=t-butyl) and (III) (R=t-butyl) were 4.0 minutes and 3.1 minutes respectively.

On completion of the bioreduction stage the fermentation broth was centrifuged at 5000 rpm for 20 minutes at 20–22° C. The compound of formula (III) (R=t-butyl) was isolated from the supernatant by extraction with a suitable organic solvent such as toluene, isoamyl acetate, 2-pentanone, ethyl acetate or 4-methyl-2-pentanone, preferably ethyl acetate or 2-pentanone. The solvent extract was dried over anhydrous sodium sulphate and the solvent removed by vacuum distillation to afford the crude product of formula III (R=t-butyl) as a golden oil.

The ratio of the compound of formula (III) (R=t-butyl) to its diastereoisomer (IV) (R=t-butyl) was either measured by HPLC of the crude product following the procedure described in Example 1 or by HPLC measurement of the ratio of the corresponding iso-propylidene derivatives (I) and its diastereoisomer (V)

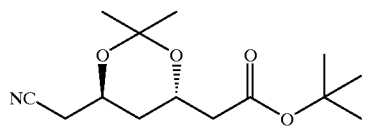

under the following conditions:
HPLC: Hewlett Packard HP 1050
Column: YMC ODS AQ303 4.6×250mm dimension and 5 μm particle size. Available from Hichrom Limited.
Solvent: Methanol:water (50:50)
Flow rate: 1 ml/min
Detector: Hewlett Packard HP 1047A refractive index detector
Temperature: Ambient
The retention times of the compounds of formula (I) and (V) were 31.0 minutes and 35.5 minutes respectively.

EXAMPLE 4

Preparation of the Isopropylidene Derivative (I) and Its Diastereoisomer (V)

Samples of the compound of formula (III) (R=t-butyl), (IV) (R=t-butyl) and the crude product from bioreduction of the compound of formula (II) (R=t-butyl) were converted to the corresponding isopropylidene derivative by reaction with 2,2-dimethoxypropane in dry acetone in the presence of catalytic methanesulphonic acid. In a typical reaction 3 g of the crude bioreduction product was reacted with 2,2-dimethoxypropane (7 ml) in dry acetone (5 ml) containing methanesulphonic acid (5 μl) for 2 hours at ambient temperature. The solution was then poured into 15 ml of 2% w/v aqueous sodium bicarbonate and stirred for a further 5 minutes. The resulting mixture was extracted with 30 ml ethyl acetate. The ethyl acetate extract was separated, combined with 15 ml n-hexane and the combined organic extract washed with 30 ml distilled water. The organic phase was dried over anhydrous sodium sulphate and the solvent removed by vacuum distillation to afford a deep orange oil which solidified on cooling.

EXAMPLES 5–13

Preparation of the Compound of Formula (III) (R=t-butyl) Under Varying Conditions of pH, Temperature, Aeration and Fermentation Regime Examples 5–13 inclusive serve to illustrate operation of the process using *Pichia angusta* NCYC R320 in each case at an initial dry cell weight in the range 10 to 15 g/L for preparing the compound of formula (III) (R=t-butyl) from the compound of formula (II) (R=t-butyl). The process was carried out as described in Example 3 except when indicated in Table 3.

The results from operation of the process under the conditions specified in Table 3 are summarised in Table 4.

The reaction profile obtained by operation of the process under the conditions specified in Example 13 is shown in FIG. 1. The initial dry cell weight in this case was 12.67 g/L.

TABLE 3

| Example | pH | Temperature (°C.) | Aeration (vvm) | Fed-batch/batch culture |
|---|---|---|---|---|
| 5 | 5.5 | 28 | 1 | Batch |
| 6 | 5.5 | 34 | 1 | Batch |
| 7 | 5.5 | 40 | 1 | Batch |
| 8 | 5.5 | 28 | 0.1 | Batch |
| 9 | 6.5 | 28 | 1 | Batch |
| 10 | 4.5 | 28 | 1 | Batch |
| 11 | 4.5 | 34 | 1 | Batch |
| 12 | 5.5 | 28 | 1 | Fed-batch |
| 13 | 4.5 | 28 | 1 | Fed-batch |

VVM means volume of air (measured at standard temperature and pressure) per volume of culture medium per minute.

TABLE 4

| Example | Reaction time (hr) | Conversion of (II) to (III) (%) | Specific rate of reduction of (II) to (III) (g $L^{-1}h^{-1}g^{-1}$ dry cell weight) | Concentration of (III) (g/L) | yield of (III) (%) | Isolated Ratio of (I) to (V)* |
|---|---|---|---|---|---|---|
| 5 | 44 | 85 | 0.022 | 12.3 | 87 | >166:1 |
| 6 | 22 | 83 | 0.027 | 2.62 | ND | >64:1 |
| 7 | 47 | 57 | 0.052 | 6.1 | 85 | >86:1 |
| 8 | 52 | 71 | 0.025 | 7.1 | 88 | >71:1 |
| 9 | 24 | 79 | 0.032 | 4.65 | ND | >85:1 |
| 10 | 49 | 93 | 0.015 | 11.3 | 84 | >110:1 |
| 11 | 25.5 | ND | 0.018 | 1.98 | ND | >63::1 |
| 12 | 41 | 84 | 0.037 | 10.95 | 84 | >92:1 |
| 13 | 48 | 79 | 0.030 | 16.96 | 91 | >172:1 |

*Compound (V) was not detected in any of the samples prepared. Results were calculated based on the detection limit for compound (V) using the HPLC conditions described in Example 3.
ND Not determined EXAMPLE 14
Characterisation of the Compound of Formula (III) (R=t-butyl)

The crude product (III) (R=t-butyl) obtained by operation of the process as described in Example 5 was converted to its isopropylidene derivative (I) following the procedure described below:

The crude product (145 g containing 65 g of III, 0.28 mole) was placed in a 1 L roundbottom flask equipped with a magnetic stirrer. To the flask was added dry acetone (200 ml), 2,2-dimethoxypropane (294 ml, 2.39 moles) and methanesulphonic acid (1.5 ml). The pH of the solution was checked by spotting a small sample onto a piece of damp pH indicator paper to ensure it was acidic. The reaction mixture was stirred at ambient temperature and the disappearance of (III) monitored by HPLC using the procedure described in Example 3. The reaction was complete in 3 hours at which point 550 ml of 2% w/v aqueous sodium bicarbonate was added. The pH was again checked as above to ensure it was in the range 7–9. The mixture was transferred to a separating funnel and extracted with 400 ml of ethyl acetate. The ethyl acetate was removed and the aqueous re-extracted with a further 200 ml of ethyl acetate. The ethyl acetate extracts were combined and 1 L of n-hexane added. The combined ethyl acetate and hexane solution was washed with 3×1 L of distilled water and the organic phase separated and dried over anhydrous sodium sulphate. The solvent was removed by vacuum distillation to yield a red oil which solidified on cooling.

The isopropylidene (I) was crystallised from n-hexane and recrystallised from n-heptane to afford a white crystalline product in 81% yield. The iso-propylidene (I) was found to be of 98.65% chemical purity, devoid of compounds (II), (III) and (V) (R=t-butyl) and indistinguishable by both infra-red spectroscopy and 250 MHz $^1$H NMR spectrometry from an authentic sample of (I).

REFERENCES

ATCC American Type Culture Collection, 123031 Parklawn Drive, Rockville, Md. 20852 U.S.A.

CBS Centraal Bureau Voor Schimmel Cultures, Oosterstraat 1, Postbus 273, NL-3740 AG Baarn, Netherlands.

DSM Deutsche Sammlung Von Mikrooorganismen und Zellkulturen GmbH, Mascheroder Weg 1b, D-330 Braunschweig, Germany.

NCYC National Collection of Yeast Cultures Institute of Food Research, Norwich Laboratory, Norwich Research Park, Colney, Norwich NR4 7UA.

BPCC ZENECA Limited, Bioproducts Culture Collection (Not publicly available).

95TJL03S - MS - Jun. 11, 1996

I claim:
1. A process for making the compound of formula (III)

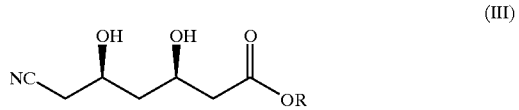

(III)

which comprises stereoselectively reducing a compound of formula (II)

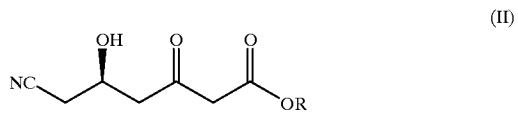

(II)

wherein R is an alkyl group, using a reductase obtainable from Beauveria, Candida, Kluyveromyces, Debaromyces or Pichia and recovering the compound of Formula (III).

2. The process as claimed in claim 1 wherein the reductase is obtainable from *Beauveria bassiana, Pichia pastoris, Pichia haplophila, Pichia membranefaciens, Candida humicola, Candida solani, Candida diddensiae, Candida friedrichii, Kluyveromyces drosophilarum, Debaromyces hansenii* or *Pichia angusta*.

3. The process as claimed in claim 1 in which the reductase is obtained from Beauveria, Candida, Kluyveromyces or Debaromyces or Pichia.

4. The process as claimed in claim 1, in which the reductase is provided by the presence of whole cells of Beauveria, Candida, Kluuveromyces, Debaromyces or Pichia during the selective reduction.

5. The process as claimed in claim 1 in which the reductase is one produced by Pichia.

6. The process as claimed in claim 5 in which the reductase is that produced by *Pichia haplophila* or *Pichia angusta*.

7. The process as claimed in claim 1 which is carried out in the presence of whole cells of an organism producing the reductase in a nutrient medium which contains a carbon source for the organism.

8. The process as claimed in claim 7 in which nitrogen and phosphorus sources and trace elements are present.

9. The process as claimed in claim 8 which is carried out under aerobic conditions.

10. A process for making the compound of formula (IV)

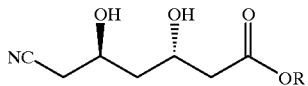

(IV)

which comprises stereoselectively reducing the compound of formula (II)

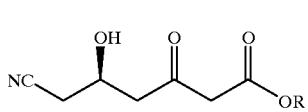

(II)

wherein R is an alkyl group, using a microbe selected from the group consisting of *Candida pelliculosa, Neurospora crassa, Pichia trehalophila* and *Hansenula anomola* or using the reductase derived from said microorganism and recovering the compound of Formula (IV).

* * * * *